United States Patent [19]

Raghu et al.

[11] 4,439,611

[45] Mar. 27, 1984

[54] **ISOLATION OF [S-(R*, S*]-1-(3-ACETYLTHIO-3-BENZOYL-2-METHYLPROPIONYL)-L-PROLINE FROM A DIASTEREOMERIC MIXTURE**

[75] Inventors: Sivaraman Raghu, Norwalk; Robert J. Proverb, Stamford; Steven L. Peake, New Canaan, all of Conn.

[73] Assignee: American Cyanamid Company, Stamford, Conn.

[21] Appl. No.: 393,002

[22] Filed: Jun. 28, 1982

[51] Int. Cl.$^3$ .......................................... C07D 207/16
[52] U.S. Cl. .................................................. 548/533
[58] Field of Search ........................................ 548/533

[56] References Cited

U.S. PATENT DOCUMENTS 4,226,775  10/1980  McEvoy et al. ...................... 548/533
4,297,282  10/1981  Ohashi et al. ....................... 548/533

Primary Examiner—Joseph Paul Brust
Attorney, Agent, or Firm—E. A. Conroy, Jr.

[57] ABSTRACT

This disclosure describes continuous epimerization-crystallization process for the isolation of [S-(R*, S*)]-1-(3-acetylthio-3-benzoyl-2-methylpropionyl)-L-proline from a diasteromeric mixture thereof with [S-(R*, R*)]-1-(3-acetylthio-3-benzoyl-2-methylpropionyl)-L-proline.

6 Claims, No Drawings

ISOLATION OF [S-(R*,S*]-1-(3-ACETYLTHIO-3-BENZOYL-2-METHYL-PROPIONYL)-L-PROLINE FROM A DIASTEREOMERIC MIXTURE

BRIEF SUMMARY OF THE INVENTION

This invention is concerned with a novel process for resolving a diastereomeric mixture of [S-(R*,S*)]-1-(3-acetylthio-3-benzoyl-2-methylpropionyl)-L-proline (I) and [S-(R*,R*)]-1-(3-acetylthio-3-benzoyl-2-methylpropionyl)-L-proline (II).

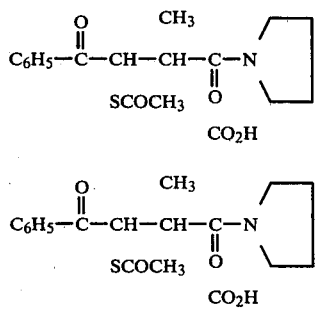

In the original synthesis of (I), as set forth in Example 12 of U.S. Pat. No. 4,226,775, the crude product is obtained as an oily mixture of diastereomers, the desired (I) and the undesired (II). The ratio of (I) and (II) varies from 1:2 to 3:1. The isolation of (I) from the mixture, as set forth in Example 69 of U.S. Pat. No. 4,226,775, was originally accomplished by sequential column chromatography, high pressure liquid chromatography, and a final slow crystallization in low yields. This procedure is completely impractical for scale-up to prepare larger quantities of material.

DETAILED DESCRIPTION OF THE INVENTION

An alternative procedure for the isolation of (I) from a mixture of (I) and (II) has also been developed which consists of a very slow evaporative crystallization from diethyl ether followed by another slow recrystallization from n-hexane-ethyl acetate. The disadvantages of this procedure are: (a) diethyl ether cannot be used in a plant environment; (b) a initial ratio of at least 2:1 of (I):(II) is required for crystallization; (c) the process is tedious and slow; (d) yields are low; and (e) the undesired diastereomer (II) containing significant amounts of the desired diastereomer (I) has to be discarded in the mother liquors.

It has now been discovered that when a mixture of (I) and (II) is equilibrated in a specific solvent system in which (I) has limited solubility, a continuous crystallization of (I) occurs in conjunction with a continuous epimerization of (II) to (I) whereby nearly all of (II) also crystallizes out as (I). The specific solvent system operable in this novel process of the present invention consists of trifluoroacetic acid and an organic solvent in the ratio of one part of trifluoroacetic acid to from about two parts to about ten parts of organic solvent. The organic solvent may be a single compound such as chloroform, dibutyl ether, chlorobenzene, acetonitrile, ethyl acetate and the like or mixtures thereof in any proportion. The continuous epimerization-crystallization process of the present invention is carried out in the solvent system at a temperature of from about 45° C. to about 75° C. for a period of time of from about 8 to about 24 hours. At the end of this period of time, the crystallized (I) is removed by filtration, washed with n-hexane and dried.

The invention will be described in greater detail in conjunction with the following specific examples.

EXAMPLE 1

A total of 57.5 g. (0.158 mol.) of crude (I)+(II) (ratio 3:5) was dissolved in 280 ml. of di-n-butyl ether and 20.5 ml. of $CF_3CO_2H$ while heating at 50°–70° C. Once solution had been effected, seeds were added and the mixture stirred in an oil bath at about 60° C. for 24 hours. The mixture was cooled and filtered and the crystals were washed with 50 mls. of di-n-butyl ether and 100 mls. of hexane. The dry weight of the white crystalline product (I) was 32.8 g. (0.090 mol.). This represents a 57% recovery from crude product mixture, m.p. 152°–153° C, $^{13}C$ NMR analysis indicates a purity of 98+%.

EXAMPLE 2

A solution of 60.0 g. (0.165 mol.) of crude (I)+(II) was prepared by dissolution in 200 mls. of 1:5 trifluoroacetic acid:chloroform. The solution refluxed for 8 hours with seed crystals and allowed to cool. The product, (I), was filtered and washed with cold hexane. The dry weight of the white crystalline product was 27.6 g. (0.076 mol.) for a 46.1% yield.

EXAMPLE 3

A solution of 60.0 g. (0.165 mol.) of crude (I)+(II) was prepared by dissolution in 250 ml. of 1:4 trifluoroacetic acid:chlorobenzene. Seed crystals were added and the solution was heated at 65° C. for 16 hours. Upon cooling, the solid was filtered, washed with hexane and air dried. Isolated are 30.0 g. (0.082 mol.) of product I corresponding to a 49.7% yield.

EXAMPLE 4

Crude (I)+(II) 60.0 g. (0.165 mol.) was dissolved in 217 ml. of 1:3:6 trifluoroacetic acid:acetonitrile:chlorobenzene. Seeds were added and the solution heated at 55°–70° C. for 24 hours. The product, (I), was filtered after cooling, washed with hexane and air dried. Isolated were 31.3 g. (0.086 mol.), representing a 52.1% yield.

EXAMPLE 5

Crude (I)+(II) 60.0 g. (0.165 mol.) was dissolved in 1:6:6 trifluoroacetic acid:ethyl acetate:di-n-butyl ether (270 ml.). Seeds were added and the solution warmed at 65° C. for 24 hours. Product was filtered upon cooling, washed with hexane and air dried. Isolated were 29.7 g. (0.082 mol.), representing a yield of 49.7%.

We claim:

1. A process for the isolation of [S-(R*,S*)]-1-(3-acetylthio-3-benzoyl-2-methylpropionyl)-L-proline from a mixture thereof with [S-(R*,R*)]-1-(3-acetylthio-3-benzoyl-2-methylpropionyl)-L-proline which comprises dissolving the mixture in a solvent system consisting of one part of trifluoroacetic acid and from about two to about ten parts of an organic solvent inert to trifluoroacetic acid and maintaining the solution at 45°–75° C. for a period of time of 8–24 hours while the [S-(R*,S*)] isomer epimerizes to the [S-(R*,S*)] isomer and the [S-(R*,S*)] isomer crystallizes from the solution.

2. The process according to claim 1 wherein the organic solvent is di-n-butyl ether.

3. The process according to claim 1 wherein the organic solvent is chloroform.

4. The process according to claim 1 wherein the organic solvent is chlorobenzene.

5. The process according to claim 1 wherein the organic solvent is a mixture of chlorobenzene and acetonitrile.

6. The process according to claim 1 wherein the orgaic solvent is a mixture of ethyl acetate and di-n-butyl ether.

* * * * *